United States Patent [19]
Zdarsky

[11] Patent Number: 5,127,832
[45] Date of Patent: Jul. 7, 1992

[54] MEASURING HANDLE FOR TREATING DENTAL ROOT CANALS

[75] Inventor: Eduard Zdarsky, Palm Beach, Fla.

[73] Assignee: Vereinigte Dentalwerke Antaeos-Beutelrock-Zipperer Zdarsky Ehrler GmbH & Co. KG, Munich, Fed. Rep. of Germany

[21] Appl. No.: 601,759

[22] PCT Filed: Apr. 12, 1989

[86] PCT No.: PCT/DE89/00217

§ 371 Date: Oct. 19, 1990

§ 102(e) Date: Oct. 19, 1990

[87] PCT Pub. No.: WO89/10097

PCT Pub. Date: Nov. 2, 1989

[30] Foreign Application Priority Data

Apr. 21, 1988 [DE] Fed. Rep. of Germany ....... 3813474

[51] Int. Cl.⁵ .......................... A61C 5/02; A61C 3/00; A61C 19/04
[52] U.S. Cl. ..................... 433/102; 433/147; 433/72
[58] Field of Search .................. 433/72, 102, 141, 147

[56] References Cited

U.S. PATENT DOCUMENTS

| | | | |
|---|---|---|---|
| 1,620,990 | 3/1927 | Brothers | 433/147 |
| 3,247,594 | 4/1966 | Nosonowitz | 433/102 |
| 3,324,555 | 6/1967 | Zdarsky | 433/102 |
| 3,562,913 | 2/1971 | Saffro | 433/75 |
| 3,713,221 | 1/1973 | Malmin | 433/75 |
| 3,924,334 | 12/1975 | Lentine et al. | 433/102 |
| 4,251,214 | 2/1981 | Schnall | 433/147 |
| 4,582,489 | 4/1986 | Listl | 433/102 |

FOREIGN PATENT DOCUMENTS

0007959 2/1980 European Pat. Off. .
929867 of 0000 Fed. Rep. of Germany .

Primary Examiner—Cary E. O'Connor
Assistant Examiner—Cindy A. Cherichetti
Attorney, Agent, or Firm—Herbert Dubno

[57] ABSTRACT

A measuring handle for treating dental root canals comprises a handle in which an instrument slides longitudinally. The guide hook of the instrument engages in a helical screw rotatably mounted in the handle and is guided longitudinally in a longitudinal slot in the handle. The handle is expanded at its rotating end to form a gripping head in which is arranged a cylindrical mounting space for a rotary body of a rotary handle which actuates the helical screw. A section of the longitudinal slot expands through the rotary handle into the gripping head and is covered in the region of said slot, so that, in a development of the handle having an additional gripping head at the end nearer the instrument, the head can be firmly gripped when gloves are worn or the handle is wet with water or saliva.

18 Claims, 1 Drawing Sheet

MEASURING HANDLE FOR TREATING DENTAL ROOT CANALS

FIELD OF THE INVENTION

The invention relates to a measuring handle for treating dental root canals.

THE RELATED ART

In the case of root canal instruments, such as drills, files, probes, etc., it is known to set them to a certain depth by means of a handle. Thereby, the handle can also have a graduated scale. In a measuring handle of this kind (DE AS 1 280 469), it is known to guide the instrument holder in the handle only longitudinally slidable, for this purpose the holder end being bent into a guide hook which is movable in a longitudinal slot of the handle. The sliding motion of the instrument is caused by a helical coil rotatably supported in a hollow cylinder space in the handle. In order to rotate this helical coil, a rotary disc is provided at the free handle end, which has only to be rotated correspondingly to set the depth level, in order to slide the instrument in the handle forward or backwards. Since the pitch of the helical coil is set to be self-locking, the instrument is locked in any position. Furthermore, the helical coil is so designed that its windings snugly surround the instrument holder and the superposed coil threads snugly surround the hook part, so that the instrument can be guided without shaking. In order to rotate the coil, the upper coil end engages in the rotary disk which is supported in a groove of the handle housing. This rotary disk is also provided with a slot, through which the instrument can be inserted into or removed from the handle. In the case of this known measuring handle, the handle is made of metal, whereby not only high manufacturing costs result, but also the surface configuration of the handle is limited. In order to get a secure grip on the handle, a number of annular knurls are provided, so that to a certain extent it can be guided securely with the bare fingers. However, these known measures do not suffice when the measuring handle has to be handled with gloves. It is therefore the object of the invention to improve a measuring handle for the treatment of dental root canals of the aforementioned kind, so that it can be sufficiently securely guided and the instrument can be set also when wearing gloves.

SUMMARY OF THE INVENTION

The object of the invention has been achieved through provision of a measuring handle for treatment of dental root canals which comprises:
- a handle casing having therein a cylindrical hollow space;
- a helical coil rotatably supported in the cylindrical hollow space;
- an instrument longitudinally adjustable relative to a length of the handle casing, the instrument being supported within the helical coil and including a guide hook at an end thereof engaging the helical coil to thereby allow transmission of a sliding motion from the helical coil to the instrument;
- a longitudinal slot provided within the handle casing for receiving the guide hook and for providing guidance for longitudinal movement thereto;
- a gripping bead formed in the handle casing surrounding an open end thereof bulging radially outward therefrom and having a top and a bottom edge defining a length of the gripping bead;
- a cylindrical bearing space formed in an area surrounded by the gripping bead;
- a rotary handle positioned at the open end of the handle casing, which includes:
  - a knob at one end of the rotary handle and resting on the top edge of the gripping bead; and
  - a rotary body supported within the cylindrical bearing space and connected with each of the knob and the helical coil for transmission of a rotary movement; and
- a slot extension longitudinally traversing the rotary handle form the top to the bottom edge adjacent along a length of the cylindrical bearing space for insertion and removal of the instrument from the handle casing.

A gripping bead at the one end of a handle offers a secure hold for a gloved hand, even when the handle is wet with water or saliva. Primarily gripping beads provided at both handle ends allow the handle, and together therewith the inserted instrument, to be securely guided up and down, because the gripping beads create perceivably thicker portions with respect to the middle portion of the handle. In such a gripping bead, it is also possible to accommodate advantageously a rotary handle with its rotary body. Thereby, the required extension of the longitudinal slot in the handle can remain covered on the outside by the rotary handle. The covering handle prevents the end of the guide hook from being blocked by the hand in this area during the insertion or removal of the instrument. If the handle is made of a moldable plastic material, it becomes possible to manufacture it in this shape with particular precision and little expense, in addition providing it with a surface permitting a firm grip.

With a precisely positioned knob a better longitudinal adjustment of the instrument is achieved, whereby the conically shaped and longitudinally ribbed knob makes possible an easy adjustment of the instrument also with gloves.

A handle made of plastic material can also be provided in a simple manner with multiple coding, in order to facilitate the dentist's work. So for instance the measuring scale can be done by point coding. If the knob is made in a different color, it can signal the fact that it belongs to a certain work place.

When the outwardly open longitudinal slot is so designed that it can also be felt with a gloved hand, an important orientation means is created for special treatment cases, such as crooked root canals. A correspondingly bent root canal instrument can be fastened in the handle with reference to this orientation mark and the instrument can be correspondingly introduced in the root canal.

As a result of its enlarged diameter, particularly due to the gripping bead, this measuring handle also offers a considerably improved X-ray contrast, primarily then when the frontal surface of the handle on the instrument side is designed to be plane, i.e. at a right angle to the instrument. In this case, the instrument can be precisely set for the radiodontia and after that the set depth can be precisely controlled.

BRIEF DESCRIPTION OF THE DRAWING

The invention will now be described in more detail with the aid of an embodiment example illustrated in the drawing which shows.

DETAILED DESCRIPTION

Figure 1:
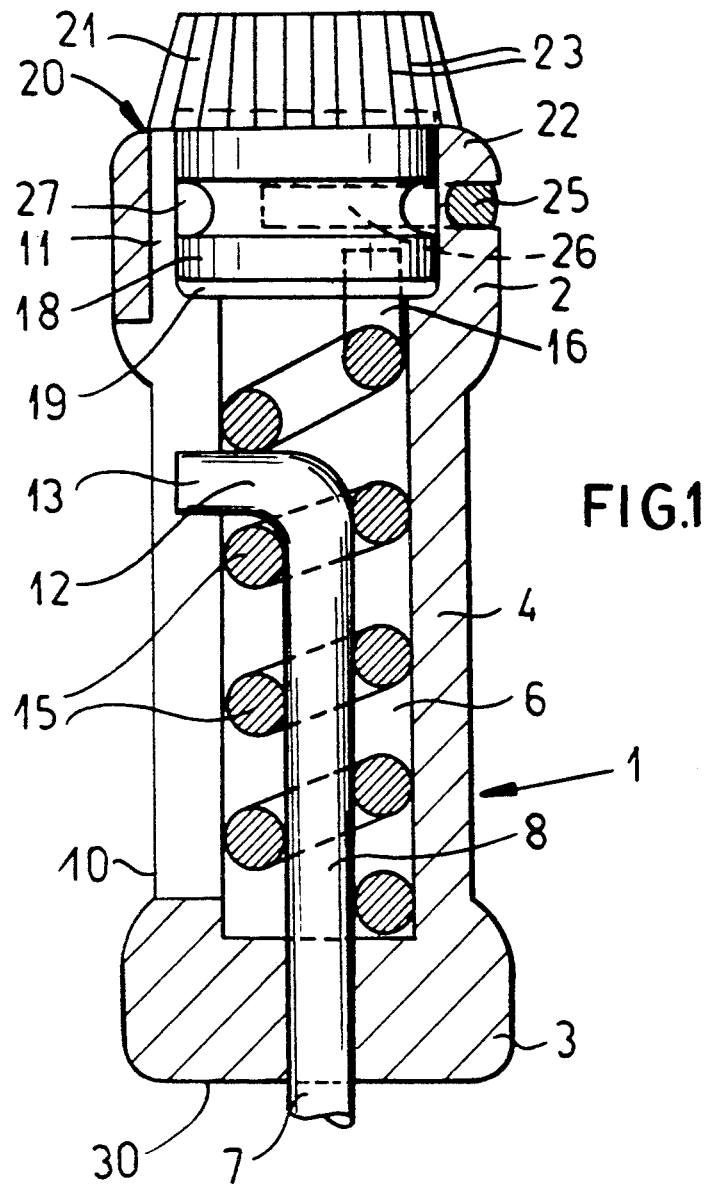
FIG. 1 a longitudinal section through a measuring handle.
Figure 2:
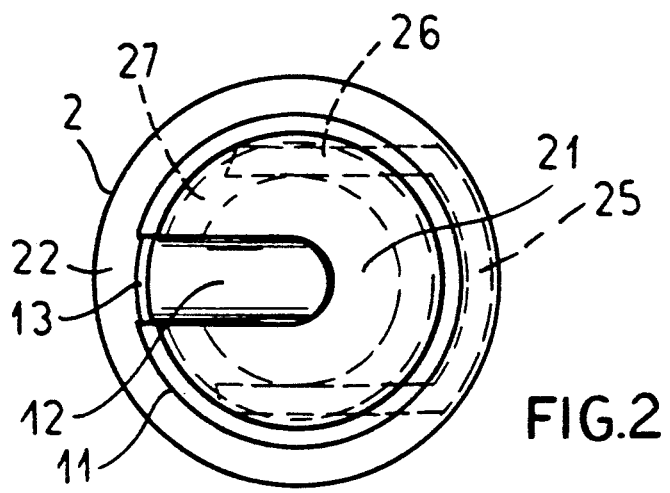
FIG. 2 a top view thereof.

The shown measuring handle has an essentially cylindrical handle 1 with an upper gripping bead 2 and a lower gripping bead 3. These two gripping beads have a diameter which is considerably enlarged with respect to the diameter of the middle portion 4, so that the gripping beads constitute good impact surfaces for the pushing and pulling motions occurring during the treatment interventions. Inside the handle, a hollow cylindrical space is formed, whereinto a treatment instrument 7 reaches with its holder 8. Along an outer shell line, the handle has a longitudinal slot 10, which has a through-going opening only on the gripping side facing away from the point of the instrument, which means that it extends also through the upper gripping bead 2 by a longitudinal slot extension 11. The width of this guide slot corresponds to the thickness of the material of the instrument holder 8, which at its free end is bent to form a guide hook 12. Since this guide hook is slidable in the longitudinal slot, the instrument can also be pulled out from the handle at the upper open end of the slot. The end of the guide hook which, as much as possible, does not protrude from the longitudinal slot, is marked with the numeral 13. Inside the hollow cylindrical space a helical coil 15 is rotatably mounted. The guide hook 12 of the instruments reaches through this coil and is moved up and down as a result of its rotating motions. In order to afford good support and guidance of the instrument, the helical coil 15 is designed so that the windings snugly surround the instrument holder and the superposed coil threads snugly surround the hook part 12. This way, it is possible to guide the instrument as much as possible free of shaking. In order to run the coil, an upper coil end 16 engages in a rotary body 18, which is rotatably supported in a cylindrical bearing space 19 of the upper gripping bead 2. The rotary body forms together with a knob 21 a rotary handle 20. The knob is located on top of the edge 22 of the gripping bead, is conically shaped and provided with longitudinal ribbing 23. The rotary handle 20 and its rotary body 18 are secured against axial displacement by a U-shaped bracket 25 made of metal. Its rotatability with respect to this U-shaped bracket inserted in the gripping bead is safeguarded by its lug 26 engaging in an annular groove 27 of the rotary body. The conical configuration of the knob 21 is particularly advantageous when the knob is provided with longitudinal ribbing, insuring a secure grip and handling by the fingers. Thereby, the resilient surface of this knob prevents an undesired rotation. Since during filing motions with the instrument, the measuring handle is rotated clockwise as well as counterclockwise, it is important that the knob not be loosened, so that the locking to the set canal depth can not be unintentionally changed. The longitudinal-slot extension 11 extends also through this knob, for the insertion and removal of the instrument.

In the shown measuring handle, the helical coil 15 has a round cross section, whereby the friction and wear-exposed surfaces between the instrument holder and the coil surface are minimized. In order to achieve a self-locking effect between these two components, the pitch of the coil is kept correspondingly low. The instrument displacement on the handle 1 is indicated by the end 13 of the guide hook. A measuring scale, also in point form, can be provided outside on the handle. It is advantageous to shorten the guide hook so that its end 13 does not project over the handle circumference, but is kept considerably below this surface. This way the displacements of the instrument are not hindered by the gloved fingers, also an unconscious displacement of the hook and thereby of the instrument is not possible. A shortened guide hook can not damage even the thin gloves.

An improved X-ray contrast results also from the increased diameter of the measuring handle due to the gripping beads, when the frontal surface of the handle on the instrument side is designed as a plane impact surface (30) which runs at a right angle to the instrument.

We claim:

1. A measuring handle assembly for the treatment of dental root canals comprising:
    a handle,
    an instrument longitudinally adjustable in said handle,
    a helical coil rotatably supported in a cylindrical hollow space of said handle for transmission of sliding motion to the instrument, a guide hook at a holder end of the instrument engaging in the helical coil,
    a longitudinal slot provided in the handle for the longitudinal guidance of the guide hook,
    a rotary handle member rotatably supported at a free end of the handle and in connection with the helical coil for the transmission of rotation,
    a longitudinal-slot extension through the rotary handle for the insertion and removal of instruments into and from the handle,
    at the end of the rotary handle, the handle being enlarged to form a gripping bead, wherein a cylindrical bearing space for a rotary body is formed, and the longitudinal-slot extension extends through the rotary handle also to the gripping bead, in whose area the longitudinal-slot extension is covered toward the outside, a rotary body of the rotary handle being secured in the gripping bead by means of a U-shaped bracket formed with lugs, said lugs engaging in an annular groove of the rotary body.

2. A measuring handle assembly as defined in claim 1 wherein the rotary handle has a knob formed on the rotary body and which sits on the gripping bead and is conically tapered towards the outside.

3. A measuring handle assembly as defined in claim 1 wherein the handle, at an end thereof opposite an end having the gripping bead is provided with a further gripping bead.

4. The measuring handle assembly as defined in claim 3 wherein the handle with its gripping beads as well as the rotary handle consist of molded plastic parts.

5. A measuring handle assembly as defined in claim 4 wherein the handle and the rotary handle have differently colored surfaces.

6. A measuring handle assembly as defined in claim 3 wherein the further gripping bead on a side thereof distant from the rotary handle forms an impact plane which is at a right angle with respect to the inserted instrument.

7. A measuring handle assembly as defined in claim 1 wherein the longitudinal slot is a gripping slot serving for orientation assistance when the instrument is inserted.

8. A measuring handle assembly as defined in claim 1 wherein the handle and/or the gripping beads are provided with longitudinal ribs.

9. A measuring handle assembly as defined in claim 1 wherein the rotary handle includes a knob having ribbing running in a longitudinal direction.

10. A measuring handle for treatment of dental root canals comprising:
- a handle casing having therein a cylindrical hollow space;
- a helical coil rotatably supported in said cylindrical hollow space;
- an instrument longitudinally adjustable relative to a length of said handle casing, said instrument being supported within said helical coil and including a guide hook at an end thereof engaging said helical coil to thereby allow transmission of a sliding motion to said instrument;
- a longitudinal slot provided within said handle casing for receiving said guide hook and for providing guidance for longitudinal movement thereto;
- a gripping bead formed in said handle casing surrounding an open end thereof bulging radially outward therefrom and having a top and a bottom edge defining a length of said gripping bead;
- a cylindrical bearing space formed in an area surrounded by said gripping bead;
- a rotary handle positioned at said open end of said handle casing, which includes:
    - a knob at one end of said rotary handle and resting on said top edge of said gripping bead; and
    - a rotary body supported within said cylindrical bearing space and connected with each of said knob and said helical coil for transmission of a rotary movement; and
    - a slot extension longitudinally traversing said rotary handle from said top to said bottom edge adjacent along a length of said cylindrical bearing space for insertion and removal of said instrument from said handle casing; and
- a U-shaped bracket formed with lugs defining sides of said bracket and wherein said rotary body is formed with an annular groove, said rotary body being secured by means of said lugs of said U-shaped bracket to said gripping bead.

11. A measuring handle according to claim 10 wherein said knob is conically tapered radially outward.

12. A measuring handle according to claim 10 further comprising another gripping bead bulging radially outward from said handle casing at an end thereof distant from said open end of said handle casing.

13. A measuring handle according to claim 12 wherein said longitudinal slot is positioned between said gripping beads and serves for assisting orientation when said instrument is inserted therein.

14. A measuring handle according to claim 12 wherein at least one of said gripping beads is provided with longitudinal ribs.

15. A measuring handle according to claim 12 wherein said further gripping bead at said end distant from said open end of said handle casing has a surface forming an impact plane which is at right angle with respect to said instrument when inserted in said measuring handle.

16. A measuring handle according to claim 10 wherein said knob has ribbing formed on an outer surface thereof which runs in a longitudinal direction.

17. A measuring handle according to claim 10 wherein said gripping bead and rotary handle are formed of molded plastic.

18. A measuring handle according to claim 17 wherein said handle casing and said rotary handle have differently colored surfaces.

* * * * *